US008367640B2

(12) United States Patent
Soula et al.

(10) Patent No.: US 8,367,640 B2
(45) Date of Patent: *Feb. 5, 2013

(54) COMPLEX CONSISTED OF A POLYSACCHARIDE AND AN HBP

(75) Inventors: Olivier Soula, Meyzieu (FR); Remi Soula, Lyons (FR); Martin Gaudier, Lyons (FR); Gerard Soula, Meyzieu (FR)

(73) Assignee: Adocia, Lyons (FR)

( * ) Notice: Subject to any disclaimer, the term of this patent is extended or adjusted under 35 U.S.C. 154(b) by 412 days.

This patent is subject to a terminal disclaimer.

(21) Appl. No.: 12/585,886

(22) Filed: Sep. 28, 2009

(65) Prior Publication Data
US 2010/0184965 A1   Jul. 22, 2010

Related U.S. Application Data

(60) Provisional application No. 61/136,705, filed on Sep. 26, 2008.

(30) Foreign Application Priority Data

Sep. 26, 2008 (FR) ...................... 08 05321

(51) Int. Cl.
A01N 43/04 (2006.01)
A01N 61/00 (2006.01)
A61K 31/715 (2006.01)
A61K 31/00 (2006.01)
(52) U.S. Cl. ................. 514/59; 514/54; 514/1
(58) Field of Classification Search ............ 514/59, 514/54, 1
See application file for complete search history.

(56) References Cited

FOREIGN PATENT DOCUMENTS

| FR | 05 09803 | 3/2007 |
| WO | WO 02/058718 A2 | 8/2002 |
| WO | WO 2007/034320 A2 | 3/2007 |
| WO | WO 2007/116143 A1 | 10/2007 |
| WO | WO 2008/038111 A1 | 4/2008 |
| WO | WO 2008/120085 A2 | 10/2008 |
| WO | WO 2009/016131 A1 | 2/2009 |

OTHER PUBLICATIONS

Machine translation of WO 2007/034320 (2007) using Microsoft Translator [online] [Retrieved Apr. 12, 2012] Retrieved from the internet <http://www.wipo.int/patentscope/search/en/detail.jsf>.*
Lauer, G., Sollberg, S., Cole, M., Krieg, T., Eming, S.A. (2002) Generation of a novel proteolysis resistant vascular endothelial growth factor 165 variant by a site-directed mutation at the plasmin sensitive cleavage site. FEBS Letters, vol. 531, p. 309-313.*
Ando, H.Y. and Radebaugh, G.W. (2000) "Preformulation" in Remington: The Science and Practice of Pharmacy, 20th Edition. Edited by Alfonso R. Gennaro. p. 704-712.*
Lustig et al., "Processing of PDGF gene products determines interactions with glycosaminoglycans," Journal of Molecular Recognition, 1999, vol. 12, pp. 112-120.
Rouet et al., "Heparin-like synthetic polymers, named RGTAs, mimic biological effects of heparin in vitro," Journal of Biomedical Materials Research, 2006, vol. 78A, pp. 792-797.
Logert-Avramoglou et al., "Interaction of specifically chemically modified dextrans with transforming growth factor β1: potentiation of its biological activity," Biomedical Pharmacology, 2002, vol. 63, pp. 129-137.
Bernfield et al., "Functions of Cell Surface Heparan Sulfate Proteoglycans," Annu. Rev. Biochem., 1999, vol. 68, pp. 729-777.
Garcia-Olivas et al., "Differential binding of platelet-derived growth factor isoforms to glycosaminoglycans," Histochem Cell Biol., 2003, vol. 120, pp. 371-382.
Jul. 1, 2009 Search Report for French Patent Application No. 0805321 (with English translation).

* cited by examiner

*Primary Examiner* — Scarlett Goon
(74) *Attorney, Agent, or Firm* — Oliff & Berridge, PLC

(57) ABSTRACT

The invention relates to a complex consisted of a polysaccharide and an HBP, said polysaccharide being consisted from glycoside bonds of (1,6) and/or (1,4) and/or (1,3) and/or (1,2) type and functionalized with at least one salifiable or salified tryptophan derivative. The invention also relates to a pharmaceutical composition comprising a complex according to the invention and to the use of a polysaccharide consisted of glycoside bonds of (1,6) and/or (1,4) and/or (1,3) and/or (1,2) type and functionalized with at least one salifiable or salified tryptophan derivative, for the preparation of a pharmaceutical formulation of stable HBPs.

12 Claims, No Drawings

COMPLEX CONSISTED OF A POLYSACCHARIDE AND AN HBP

The present invention relates to the formulation of therapeutic proteins and more particularly to the formulation of proteins that bind to heparin, known as Heparin-Binding Proteins, HBPs, which are associated, in vivo, with heparin in the form of a complex, which stabilizes them and maintains their in vivo activity.

Heparin is a natural polysaccharide bearing carboxylate and sulfate functions, whose overall charge is anionic. However, this polysaccharide is known for its anticoagulant activity since it intervenes in the formation of a complex between thrombin and antithrombin III, and this anticoagulant activity is not compatible with therapeutic use, for example in cicatrization, growth regulation or bone reconstruction treatments.

Some of these HBPs have been the subject of pharmaceutical development. However, these proteins are known to be physically unstable (aggregation) and chemically unstable (enzymatic or chemical degradation). This instability may be manifested in the formulations and/or at the site of administration. It may cause immunological reactions or a loss of efficacy. To compensate for the loss of activity, solutions such as increasing the doses or the frequency of administration are employed. They are unsatisfactory, especially on account of the high cost of these proteins.

For example, the company Genentech developed a VEGF formulation for cicatrizing foot ulcers in diabetics. A first clinical study in which the administration of the treatment was performed every two days took place. The second study was performed with a daily administration, undoubtedly to answer the problem of the duration of action of VEGF, which is too short for application every two days.

It was moreover demonstrated that it is possible to form complexes between a growth factor and a polymer, with the aim of stabilizing it, increasing its solubility and/or increasing its activity.

Thus, in patent FR 05/09803 from the Applicant, it was demonstrated that the formation of a complex between PDGF-BB in its short form and a polymer makes it possible especially to increase the solubility of this highly hydrophobic protein.

However, PDGF-BB in its short form binds 100 times less than PDGF-AA to heparin, Lustig F. et al., Journal of Molecular Recognition, 1999, 12, 112-120; it therefore cannot be considered as a growth factor belonging to the HBP family.

In the case of FGF, which is known to be relatively hydrophilic, it was demonstrated that the formation of a complex with a polymer can promote its cellular activity Rouet et al., Journal of Biomedical Materials research, 2006, 78A, 792-797, but the polymers used were sulfated since they were functionalized with benzylamine sulfate and thus had anticoagulant activity incompatible with a pharmaceutical formulation.

Logeart-Avramoglou D. et al. also describe dextrans modified with benzylamine and/or sulfates in the article Biomedical Pharmacology 2002, 63, 129-137. These polymers in solution form complexes with TGF beta 1 as demonstrated in a test of interaction by gel electrophoresis. However, the non-sulfated polymers do not show any real interaction even at ratios higher than 2000. In the case of sulfated polymers, an interaction could be demonstrated for highly sulfated polymers that have anticoagulant properties.

In addition, it is also known that benzylamine may have a certain level of toxicity and may be harmful to the biocompatibility of the polymers described in the patent mentioned previously.

The galenical formulation of therapeutic proteins must necessarily meet demands in terms of harmlessness of the excipients, and to satisfy these demands, it is essential to use compounds that are biocompatible, but also to limit the amount thereof relative to the active principle.

HBPs belong to eight families of proteins, they have very different sizes, biochemical properties and activities, but they are all capable of combining with heparin in the form of a complex, Bernfield M. et al., Annu. Rev. Biochem., 1999, 68, 729-777.

Among these proteins are proteins belonging in particular to the following families:
hormones,
growth factors.

These various families may be defined as follows.

The term "hormones" means messenger proteins produced by the endocrine system. These proteins then act remotely after having been conveyed throughout the whole organism by the blood or lymph or exterior thereto. Among the hormones are growth hormone (hGH: human growth hormone) and parathyroid hormone (PTH).

The term "growth factors" means proteins normally produced in the body, which stimulate the proliferation or differentiation of cells. Among these are proteins such as transforming growth factor β1 and 2 (TGF-β), insulin-like growth factor 2 (IGF-2), heparin binding EGF-like growth factor (HB-EGF), fibroblast growth factors 1 to 14 (FGF), keratinocyte growth factor (KGF), nerve growth factor beta (NGF-beta), connective tissue growth factor (CTGF), placental growth factor (PlGF), R-spondins 1 to 4 and vascular endothelial growth factors A and B (VEGF).

All the complexes described were prepared with polymers having structural or biological similarity to heparin.

The problem solved by the present invention is that it has identified a very limited family of biocompatible polysaccharides that are capable of forming complexes with HBPs in order, inter alia, to stabilize them and to increase their solubility, without this polymer having the anticoagulant biological activity of heparin.

Furthermore, it has been observed that, to increase the affinity of the polysaccharide for proteins and its selectivity toward HBPs, it is not necessary to further increase the amphiphilic nature of the polymer, in contrast with the solution outlined in patent application FR 05/09803.

Furthermore, to counterbalance an excessive hydrophobicity, a solution outlined in the patent application cited above consisted in grafting hydrophilic groups X or Y onto the polysaccharide chains in addition to the hydrophilic groups.

These results are all the more surprising since, by grafting a salifiable or salified hydrophobic group such as a tryptophan residue, which bears an acid function, the affinity of the polysaccharide for the protein and the selectivity toward HBPs are increased, without reducing the number of carboxyl functions in the starting polysaccharide.

By means of the choice of these substituents, the selectivity toward HPBs is considerably increased.

The invention thus relates to the use of a polysaccharide substituted with a tryptophan or a tryptophan derivative, said tryptophan or tryptophan derivative being salifiable or salified, for the stabilization of HBPs.

The invention more particularly relates to the use of said polysaccharide for the preparation of a pharmaceutical formulation of stable HBPs.

The invention also relates to a complex consisted of a polysaccharide and an HBP.

The polysaccharides according to the invention are consisted of glycoside bonds of (1,6) and/or (1,4) and/or (1,3) and/or (1,2) type. They may be neutral, i.e. not bearing acidic or anionic functions, i.e. bearing acid functions.

They are functionalized with at least one tryptophan residue or one tryptophan derivative, noted Trp:

said tryptophan derivative being grafted or bound to the polysaccharides via coupling with an acid function, said acid function possibly being an acid function of an anionic polysaccharide and/or an acid function borne by a linker R bound to the polysaccharide via a function F, said function F resulting from coupling between the linker R and an —OH function of the neutral or anionic polysaccharide, F being an ester, thioester, amide, carbonate, carbamate, ether, thioether or amine function, R being a chain containing between 1 and 18 carbon atoms, which is optionally branched and/or unsaturated, comprising one or more heteroatoms, such as O, N and/or S, and having at least one acid function, Trp being a tryptophan residue or a tryptophan derivative, L or D, produced by coupling between the amine of tryptophan and at least one acid borne by the group R and/or an acid borne by the anionic polysaccharide, said tryptophan or tryptophan derivative being salifiable or salified.

In one embodiment, Trp is a tryptophan residue, or tryptophan derivative, of D-configuration.

In one embodiment, Trp is a tryptophan residue, or tryptophan derivative, of L-configuration.

The HPB is chosen from the group:

hormones, for instance growth hormone (hGH: human growth hormone) or parathyroid hormone (PTH), growth factors, for instance proteins such as transforming growth factors β1 and 2 (TGF-β) insulin-like growth factor 2 (IGF-2), heparin-binding EGF-like growth factor (HB-EGF), fibroblast growth factors (FGF) of type 1 to 14, keratinocyte growth factor (KGF), nerve growth factor β (NGF-β), connective tissue growth factor (CTGF), placental growth factor (PlGF), R-spondins 1 to 4 and vascular endothelial growth factors A and B (VEGF).

According to the invention, the functionalized polysaccharides may correspond to the following general formulae:

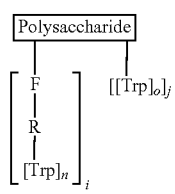

Formula I

F resulting from coupling between the linker R and an —OH function of the neutral or anionic polysaccharide, being an ester, thioester, amide, carbonate, carbamate, ether, thioether or amine function, R being a chain containing between 1 and 18 carbons, optionally branched and/or unsaturated, comprising one or more heteroatoms, such as O, N and/or S, and having at least one acid function, Trp being a tryptophan-based residue, L or D, produced from coupling between the amine of the tryptophan or of tryptophan derivative and at least one acid borne by the group R and/or an acid borne by the anionic polysaccharide, said tryptophan or tryptophan derivative being salifiable or salified, n represents the mole fraction of R substituted with Trp and is between 0.2 and 0.7, o represents the mole fraction of acid functions of the polysaccharides substituted with Trp and is between 0.2 and 0.7, i represents the mole fraction of acid functions borne by the group R per saccharide unit and is between 0 and 2, j represents the mole fraction of acid functions borne by the anionic polysaccharide per saccharide unit and is between 0 and 1, (i+j) represents the mole fraction of acid functions per saccharide unit and is between 0.5 and 2, when R is not substituted with Trp, then the acid(s) of the group R are carboxylates of a cation, preferably an alkali metal cation such as $Na^+$ or $K^+$, when the polysaccharide is an anionic polysaccharide, when one or more acid functions of the polysaccharide are not substituted with Trp, then they are salified with a cation, preferably of an alkali metal such as Na or K, said polysaccharides being at neutral pH.

In one embodiment, F is an ester, a carbonate, a carbamate or an ether.

In one embodiment, the polysaccharide is consisted in majority of glycoside bonds of (1,6) type.

In one embodiment, the polysaccharide consisted in majority of glycoside bonds of (1,6) type is a dextran.

In one embodiment, the polysaccharide is consisted in majority of glycoside bonds of (1,4) type.

In one embodiment, the polysaccharide consisted in majority of glycoside bonds of (1,4) type is chosen from the group consisting of pullulan, alginate, hyaluronan, xylan, galacturonan and a water-soluble cellulose.

In one embodiment, the polysaccharide is a pullulan.
In one embodiment, the polysaccharide is an alginate.
In one embodiment, the polysaccharide is a hyaluronan.
In one embodiment, the polysaccharide is a xylan.
In one embodiment, the polysaccharide is a galacturonan.
In one embodiment, the polysaccharide is a water-soluble cellulose.
In one embodiment, the polysaccharide is consisted in majority of glycoside bonds of (1,3) type.
In one embodiment, the polysaccharide consisted in majority of glycoside bonds of (1,3) type is a curdlan.
In one embodiment, the polysaccharide is consisted in majority of glycoside bonds of (1,2) type.
In one embodiment, the polysaccharide consisted in majority of glycoside bonds of (1,2) type is an inulin.
In one embodiment, the polysaccharide is consisted in majority of glycoside bonds of (1,4) and (1,3) type.
In one embodiment, the polysaccharide consisted in majority of glycoside bonds of (1,4) and (1,3) type is a glucan.
In one embodiment, the polysaccharide is consisted in majority of glycoside bonds of (1,4), (1,3) and (1,2) type.
In one embodiment, the polysaccharide consisted in majority of glycoside bonds of (1,4), (1,3) and (1,2) type is mannan.
In one embodiment, the polysaccharide according to the invention is characterized in that the group R is chosen from the following groups:

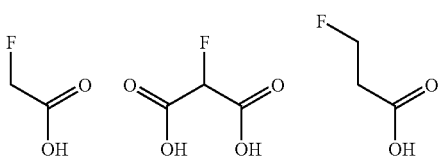

or the alkali metal cation salts thereof.

In one embodiment, the polysaccharide according to the invention is characterized in that the tryptophan or tryptophan derivative is chosen from the group consisting of tryptophan, tryptophanol, tryptophanamide and 2-indole ethylamine, and the alkali metal cation salts thereof.

This tryptophan substituent or tryptophan derivative substituent is a salifiable or salified substituent, i.e. it bears at least one anionic or cationic hydrophilic function, i.e. an acid, alcohol or amine capable of giving carboxylates, alkoxides or amine salts.

The polysaccharide may have a degree of polymerization m of between 10 and 10 000.

In one embodiment, it has a degree of polymerization m of between 10 and 1000.

In another embodiment, it has a degree of polymerization m of between 10 and 500.

In one embodiment, the complex according to the invention is characterized in that the polysaccharide/HBP mass ratio is between 0.5 and 500 and preferably between 1 and 300.

In one embodiment, the complex according to the invention is characterized in that the polysaccharide/HBP mass ratio is between 0.5 and 100 and preferably between 1 and 10.

In one embodiment, the complex according to the invention is characterized in that the HBP is chosen from the group of hormones such as growth hormone (hGH: human growth hormone) or parathyroid hormone (PTH).

In one embodiment, the complex according to the invention is characterized in that the HBP is chosen from the group of growth factors, for instance proteins such as transforming growth factor β1 and 2 (TGF-β), insulin-like growth factor 2 (IGF-2), heparin binding EGF-like growth factor (HB-EGF), fibroblast growth factors 1 to 14 (FGF), keratinocyte growth factor (KGF), nerve growth factor beta (NGF-beta), connective tissue growth factor (CTGF), placental growth factor (PIGF), R-spondins 1 to 4 and vascular endothelial growth factors A and B (VEGF).

The invention also relates to a process for preparing said polysaccharides by grafting a tryptophan derivative as defined previously onto a neutral polysaccharide, by coupling between the amine function of the tryptophan or a tryptophan derivative and an acid function obtained by grafting a group R bearing at least one acid function as defined previously onto an alcohol function of the polysaccharide, to obtain polysaccharides of formula I in which j=0.

In one embodiment, the polysaccharides according to the invention are obtained by grafting a tryptophan derivative as defined previously onto an acid function of an anionic polysaccharide, by coupling between the amine function of the tryptophan or a tryptophan derivative and an acid function borne by the anionic polysaccharide, to obtain polysaccharides of formula I in which i=0.

In one embodiment, when the polysaccharide is an anionic polysaccharide, groups R may be grafted onto the alcohol functions of the polysaccharide and the grafting of the tryptophan or a tryptophan derivative may be performed:

- either selectively on the acid functions of the groups R, to obtain polysaccharides of formula I in which o=0, via protection and deprotection reactions that are well known to those skilled in the art, or
- in combination on the two types of acid function, to obtain polysaccharides of formula I in which n>0 and o>0.

In all the embodiments described above, the coupling reactions are followed by neutralization of the acid functions that have not reacted with a tryptophan derivative, by salification via one of the methods that are well known to those skilled in the art, to obtain a salt of a cation of an alkali metal, preferably Na or K.

The invention also relates to a pharmaceutical composition comprising a complex according to the invention as described previously.

The invention also relates to a pharmaceutical composition according to the invention as described previously, wherein it is obtained by drying and/or lyophilization.

The HBP may be exogenous, i.e. it is provided by the composition according to the invention. It may also be endogenous, for example the growth factors that will be secreted into a wound during the first phase of cicatrization and that may be stabilized via formation of the complex according to the invention in vivo in the wound.

According to the pathologies targeted, it is intended for local or systemic treatment.

In the case of local and systemic releases, the modes of administration envisioned are via the intravenous, subcutaneous, intradermal, transdermal, intramuscular, oral, nasal, vaginal, ocular, buccal, pulmonary, etc. routes.

The pharmaceutical compositions according to the invention are either in liquid form, as an aqueous solution, or in the form of a powder, an implant or a film. They also comprise standard pharmaceutical excipients that are well known to those skilled in the art.

Depending on the pathologies and the modes of administration, the pharmaceutical compositions may also advantageously comprise excipients that enable them to be formulated in the form of a gel, a sponge, an injectable solution, a drinkable solution, a lyoc, etc.

The invention also relates to a pharmaceutical composition according to the invention as described previously, wherein it may be administered in the form of a stent, a film or "coating" of implantable biomaterials, or an implant.

EXAMPLES

A—Synthesis of the Polymers

Example 1

Synthesis of Sodium Dextranmethyl Carboxylate Modified with the Sodium Salt of Tryptophan, Polymer 1

70 g (i.e. 1295 mmol of hydroxyl functions) of dextran with a weight-average molar mass of about 40 kg/mol (Fluka) are dissolved in water to 42 g/L. 130 mL of 10 N NaOH (1295 mmol of NaOH) are added to this solution. The mixture is brought to 35° C., and 201 g (1727 mmol) of sodium chloroacetate are added. The temperature of the reaction medium is raised to 60° C. at 0.5° C./minute and then maintained at 60° C. for 100 minutes. The reaction medium is diluted with 200 mL of water, neutralized with acetic acid and purified by ultrafiltration on a 5 kD PES membrane against 6 volumes of water. The final solution is assayed by dry extract to determine the polymer concentration, and then assayed by acid/ base assay in 50/50 (V/V) water/acetone to determine the degree of substitution with methylcarboxylates.

According to the dry extract: [polymer]=51.5 mg/g

According to the acid/base assay: the degree of substitution of the hydroxyl functions with methylcarboxylate functions is 1.04 per saccharide unit.

The solution of sodium dextranmethyl carboxylate is passed through a Purolite resin (anionic) to obtain dextranmethylcarboxylic acid, which is then freeze-dried for 18 hours.

14.5 g of dextranmethylcarboxylic acid (i.e. 66 mmol of methylcarboxylic acid functions) are dissolved in DMF to 57 g/L and then cooled to 0° C. 6.67 g (66 mmol) of NMM and 7.15 g (66 mmol) of EtOCOCl are then added. After reaction for 10 minutes, 6.06 g (30 mmol) of TrpOH are added. The medium is then warmed to 10° C. and maintained at this temperature for 30 minutes. A solution of imidazole at 340 g/L (8.97 g, 132 mmol) in water is then added, and the reaction medium is briefly heated to 30° C. The reaction medium is then diluted with 70 ml of water, and then filtered through a porosity 1 sinter funnel and then through a porosity 3 sinter funnel, after which it is clear. The solution is ultrafiltered through a 10 kD PES membrane against 10 volumes of 0.9% NaCl solution and then 6 volumes of water. The concentration of the solution of polymer 1 is determined on the dry extract. A fraction of solution is freeze-dried and analyzed by $^1$H NMR in $D_2O$ to determine the DS of grafted tryptophan.

According to the dry extract: [polymer]=54 mg/g

According to the $^1$H NMR: the mole fraction of tryptophan-modified acids is 0.38.

Example 2

Synthesis of Sodium Pullulanmethyl Carboxylate Modified with the Sodium Salt of Tryptophan, Polymer 2

8 g (i.e. 148 mmol of hydroxyl functions) of pullulan with a weight-average molar mass of about 100 kg/mol (Fluka) are dissolved in water to 42 g/L. 15 mL of 10 N NaOH (148 mmol of NaOH) are added to this solution. The mixture is brought to 35° C., and 23 g (198 mmol) of sodium chloroacetate are then added. The temperature of the reaction medium is brought to 60° C. at 0.5° C./minute and then maintained at 60° C. for 100 minutes. The reaction medium is diluted with 200 mL of water, neutralized with acetic acid and purified by ultrafiltration on a 5 kD PES membrane against 6 volumes of water. The final solution is assayed by dry extract to determine the polymer concentration, and then assayed by acid/base assay in 50/50 (V/V) water/acetone to determine the degree of substitution with methylcarboxylate.

According to the dry extract: [polymer]=31.5 mg/g

According to the acid/base assay: the degree of substitution of the hydroxyl functions with methylcarboxylate functions is 1.17 per saccharide unit.

The sodium pullulanmethyl carboxylate solution is passed through a Purolite resin (anionic) to obtain pullulanmethylcarboxylic acid, which is then freeze-dried for 18 hours.

3.51 g of pullulanmethylcarboxylic acid (i.e. 18 mmol of carboxymethyl acid functions) are dissolved in DMF to 57 g/L and then cooled to 0° C. 1.81 g (18 mmol) of NMM and 1.94 g (18 mmol) of EtOCOCl are then added. After reaction for 10 minutes, 1.40 g (7 mmol) of TrpOH are added. The medium is then warmed to 10° C. and maintained at this temperature for 30 minutes. An imidazole solution (2.43 g, 36 mmol) at 340 g/L in water is then added, and the reaction medium is briefly heated to 30° C. The reaction medium is then diluted with 70 mL of water, and then filtered through a porosity 1 sinter funnel and then a porosity 3 sinter funnel, after which it is clear. The solution is ultrafiltered through a 10 kD PES membrane against 10 volumes of 0.9% NaCl solution and then 6 volumes of water. The concentration of the solution of polymer 2 is determined on the dry extract. A fraction of solution is freeze-dried and analyzed by $^1$H NMR in $D_2O$ to determine the DS of grafted tryptophan.

According to the dry extract: [polymer]=17.2 mg/g

According to the $^1$H NMR: the mole fraction of tryptophan-modified acids is 0.40.

Example 3

Synthesis of a Sodium Dextranmethylcarboxylate Modified with the Ethyl Ester of Tryptophan, Polymer 3

Polymer 3 is a sodium dextranmethylcarboxylate modified with the ethyl ester of L-tryptophan obtained from a dextran with a weight-average molar mass of 40 kg/mol (Pharmacosmos) according to the process described in Example 1, using the ethyl ester of L-tryptophan instead of the sodium salt of L-tryptophan.

Example 4

Synthesis of a Sodium Dextranmethylcarboxylate Modified with the Ethyl Ester of Phenylalanine, Polymer 4

Polymer 3 is a sodium dextranmethylcarboxylate modified with the ethyl ester of L-phenylalanine obtained from a dextran with a weight-average molar mass of 40 kg/mol (Pharmacosmos) according to the process described in Example 1, using the ethyl ester of L-phenylalanine instead of the sodium salt of L-tryptophan.

B—Demonstration of the Affinity of a Polymer for a Heparin-Binding Protein by Co-Electrophoresis Example 3

1/500 Protein/Polymer Ratio

Preparation of the Protein/Polymer Complex at a 1/500 Ratio 1.5 μg of protein are added to 750 μg of polymer and 15 μl of 10× migration buffer (pH 7 tris-acetate). The solution is made up to 150 μl with $H_2O$. This solution is incubated at room temperature for 20 minutes. 5 μl of this second solution containing 50 ng of protein and 25 μg of polymer are diluted in 5 μl of 1× migration buffer. Similar solutions containing only the protein or the polymer are prepared as controls.

Demonstration of the Complex Between the Protein and the Polymer

The protein/polymer solution (10 μl) is mixed with 3 μl of loading buffer (glycerol, tris-acetate and bromophenol blue in water). These 13 μl containing 50 ng of protein and 25 μg of polymer are placed in a well of a 0.8% agarose gel. The control solutions (protein or polymer alone) are deposited in a similar manner. The electrophoresis tank is closed and the generator is set at 30V. The migration lasts for 1 hour.

After migration, the gel is transferred onto a PVDF membrane by capillary action with an Apelex system, for 2 hours at room temperature. The membrane is then saturated with skimmed milk for 1 hour at room temperature, and then incubated with rabbit primary antibodies directed against the protein (overnight at 4° C.) and finally incubated with antigoat HRP rabbit secondary antibodies (1 hour at room temperature). Revelation is performed by reacting the HRP with Opti-4CN. The revelation is stopped by rinsing with water when the coloration is sufficient, since the reaction product absorbs in the visible region.

When the protein is alone or does not form a complex with the polymer, it can migrate if it is anionic, or can remain at the deposition site if it is cationic. The protein is then detected either in the loading wells, or in the form of a single spot about 0.3-0.4 cm from the deposit. When the protein forms a complex with the polymer, the complex is entrained more strongly by the charges of the polymer and moves toward the anode. It is detected in the form of a single spot 0.7 cm from the deposit.

The results obtained with polymer 1, obtained in Example 1, polymer 2, obtained in Example 2, and proteins chosen from the groups of cell adhesion proteins, hormones, clotting proteins, heparin-binding growth factors, growth factor binding proteins, cytokines and lipid-metabolizing proteins are collated in Table I below.

The results obtained with a protein that does not bind heparin (IGF-1) and polymers 1 and 2, obtained in Example 1 and in Example 2, and the results obtained with the heparin-binding proteins mentioned above and a polymer not substituted with a tryptophan, are also collated in Table I below as counterexamples.

Demonstration of the Complex Between the Protein and the Polymer

The protein/polymer solution (10 µl) is mixed with 3 µl of loading buffer (glycerol, tris-acetate and bromophenol blue in water). These 13 µl containing 50 ng of protein and 50 ng of polymer are placed in a well of a 0.8% agarose gel. The electrophoresis tank is closed and the generator is set at 30V. The migration lasts for 1 hour.

After migration, the gel is transferred onto a PVDF membrane via capillary action with an Apelex system, for 2 hours at room temperature. The membrane is then saturated with skimmed milk for 1 hour at room temperature, and then incubated with rabbit primary antibodies directed against the protein (overnight at 4° C.) and finally incubated with anti-goat HRP rabbit secondary antibodies (1 hour at room temperature). Revelation is performed by reacting the HRP with Opti-4CN. The revelation is stopped by rinsing with water when the coloration is sufficient, since the reaction product absorbs in the visible region.

When the protein is alone or does not form a complex with the polymer, it can migrate if it is anionic, or can remain at the deposition site if it is cationic. The protein is then detected either in the loading cells, or in the form of a single spot about 0.3-0.4 cm from the deposit. When the protein forms a complex with the polymer, the complex is more strongly entrained

TABLE I

| | | Polymers | | |
|---|---|---|---|---|
| Protein family | Protein | Polymer 1 (dextranmethyl carboxylate substituted with tryptophan) | Polymer 2 (pullulanemethyl carboxylate substituted with tryptophan) | Counterexample 1 (dextranmethyl carboxylate) |
| Hormones | hGH | + | + | − |
| Heparin-binding growth factor | VEGF 165 | + | + | − |
| | FGF-2 | + | + | − |
| | NGF-betaβ | + | + | − |
| Growth factor not binding heparin | IGF 1 | − | − | − |

The results obtained show that the tryptophan-substituted dextranmethyl carboxylate polymer 1 (Example 1) or the tryptophan-substituted pullulanmethyl carboxylate polymer 2 (Example 2) make it possible to form a complex with heparin binding proteins, whereas unsubstituted dextranmethyl carboxylate (Counterexample 1) does not make this possible.

The results obtained also show that dextranmethyl carboxylate that is or is not substituted with tryptophan (Example 1 and Counterexample 1) do not form a complex with growth factors that do not bind heparin.

Example 4

1/1 Protein/Polymer Ratio

Preparation of the Protein/Polymer Complex in a 1/1 Ratio 1.5 µg of protein are added to 1.5 µg of polymer and 3 µl of 10× migration buffer (pH 7 tris-acetate). The solution is made up to 60 µl with $H_2O$. This solution is incubated at room temperature for 20 minutes. 2 µl of this second solution containing 50 ng of protein and 50 ng of polymer are diluted in 8 µl of 1× migration buffer.

by the charges of the polymer and moves toward the anode. It is detected in the form of a single spot 0.7 cm from the deposit.

The results obtained with polymers 1, 3 and 4 and two growth factors, FGF-2 and NGF-beta, are collated in Table II below.

All the protein/polymer complexes are studied at a 1/1 mass ratio

TABLE II

| | NGF-beta | FGF-2 |
|---|---|---|
| Polymer 1 | + | + |
| Polymer 3 | − | − |
| Polymer 4 | − | − |

This test makes it possible to demonstrate that the interaction between polymer 1 and the HBPs is strong enough to enable reduction of the amount of polymer, which is favorable for the purpose of pharmaceutical development. Polymers 3 and 4 do not have a sufficiently strong interaction with the two HBPs tested to obtain a complex in a 1/1 ratio.

C—Demonstration of the Affinity of a Polymer for a Heparin-Binding Protein by ITC

Example 5

Interaction of PTH (1-34) with Heparin and Polymer 1

It has been demonstrated in the literature (Kamerzell, 2007) that PTH(1-84) binds to heparin with a Kd of 300 nM during an ITC experiment (isothermal titration calorimetry). Under identical conditions, we have demonstrated that PTH (1-34) interacts with heparin with a Kd of 227 nM.

Heparin is placed in the cell at a concentration of 2 µM in 4.8 mM citrate pH 5.3 and 42 mM NaCl buffer. The PTH(1-34) is placed in the syringe at a concentration of 208.6 µM. Fifty 5 µl injections were performed and the results were adjusted to a model of n independent sites, allowing a Kd of 227 nM to be calculated.

Under similar conditions, polymer 1 was placed in the cell at a concentration of 0.5 µM in 4.8 mM citrate pH 5.3 and 42 mM NaCl buffer. The PTH(1-34) is placed in the syringe at a concentration of 191 µM. Fifty 5 µl injections were performed and the results were adjusted to a model of n independent sites, which allowed a Kd of 6.9 µM to be calculated, demonstrating the interaction of polymer 1 with the PTH, this interaction being close to that of heparin.

D—Examples of formulations

Example 6

Production of a Polymer/Heparin-Binding Protein Complex

The following operations are performed in a clean room. 5 g of lyophilizate of the polymer described in Example 1, Polymer 1, are dissolved in 50 mL of water to give solution 1 (Polymer 1 concentration of 100 mg/mL). In parallel, 10 µg of VEGF lyophilizate are dissolved in 5 µL of water to give solution 2 (VEGF concentration of 2 mg/mL). 5 µL of solution 1 are mixed with 5 µL of solution 2 at room temperature to form a solution 3 containing polymer 1 at a concentration of 50 mg/mL and VEGF at a concentration of 1 mg/mL. Solution 3 is filtered through a 0.22 µm membrane to produce a sterile solution. Formation of the complex in solution 3 may be demonstrated by co-electrophoresis.

In conclusion, the complex between a polymer according to the invention and a heparin-binding protein is formed by simple mixing of aqueous solutions at room temperature, without addition of organic solvent.

Example 7

Production of a Polymer/Heparin-Binding Protein Complex

The operations described in Example 6 are performed so as to obtain a polymer 1/VEGF complex in a 1/10 ratio, using 1 µL of solution 1 made up to 5 µL with water and 5 µL of solution 2. 10 µL of a solution 4 containing polymer 1 at a concentration of 10 mg/mL and VEGF at a concentration of 1 mg/mL are obtained.

Example 8

Production of a Polymer/Heparin-Binding Protein Complex

The operations described in Example 6 are performed so as to obtain a polymer 1/VEGF complex in a 1/2 ratio, using 0.2 µL of solution 1 made up to 5 µL with water and 5 µL of solution 2. 10 µL of solution 5 containing polymer 1 at a concentration of 2 mg/mL and VEGF at a concentration of 1 mg/mL are obtained.

Example 9

Production of a Polymer/Heparin-Binding Protein Complex

The operations described in Example 6 are performed with the polymer described in Example 2, Polymer 2, and FGF-2 as heparin-binding protein. Various aqueous solutions of Polymer 2/FGF-2 complex are obtained, the Polymer 2/FGF-2 ratios of which range from 1 to 100.

Example 10

Production of a Polymer/Heparin-Binding Protein Complex

The following operations are performed in a clean room. 5 g of lyophilizate of the polymer described in Example 2, Polymer 2, are dissolved in 100 mL of water to give solution 1 (concentration of Polymer 1 of 50 mg/mL). 10 µL of this solution are introduced into a 50 µL flask. Next, 10 µg of VEGF lyophilizate are added to this solution at room temperature. The solution obtained contains polymer 2 at a concentration of 50 mg/mL and VEGF at a concentration of 1 mg/mL. This solution is clear after 15 minutes of gentle stirring, and may be filtered through a 0.22 µm membrane to produce a sterile solution. The formation of the complex in the final solution may be demonstrated by co-electrophoresis.

Conversely, the same final solution is obtained by adding 500 µg of freeze-dried Polymer 2 to 10 µL of a VEGF solution at 1 mg/mL.

In conclusion, the complex between a polymer according to the invention and a heparin-binding protein may be formed by simple addition of a lyophilizate of polymer or of protein to an aqueous solution of protein or of polymer at room temperature, without addition of organic solvent.

The invention claimed is:
1. A complex consisting of (1) a polysaccharide substituted with a tryptophan salt and (2) a heparin-binding protein (HBP), wherein the polysaccharide is a dextran functionalized with at least the tryptophan salt:
said tryptophan salt being grafted or bound to the polysaccharide via coupling with an acid function, said acid function borne by a linker R bound to the polysaccharide via a function F, said function F resulting from coupling between the linker R and an —OH function of the polysaccharide,
F being an ester, thioester, amide, carbonate, carbamate, ether, thioether or amine function,
R being a chain containing between 1 and 18 carbon atoms, which is optionally branched and/or unsaturated, containing one or more heteroatoms selected from the group consisting of O, N, S and combinations thereof, and having at least one acid function,
Trp being a residue of the tryptophan salt, L- or D-isomer, produced by coupling between the amine of tryptophan and at least one acid borne by the group R,
said HBP being selected from the group consisting of:
hormones selected from the group consisting of human growth hormone (hGH) and parathyroid hormone (PTH), and
growth factors selected from the group consisting of transforming growth factors β1 and 2 (TGF-β), insulin-like growth factor 2 (IGF-2), heparin-binding

EGF-like growth factor (HB-EGF), fibroblast growth factors (FGF) of type 1 to 14, keratinocyte growth factor (KGF), nerve growth factor β (NGF-β), connective tissue growth factor (CTGF), placental growth factor (PIGF), R-spondins 1 to 4, and vascular endothelial growth factors A and B (VEGF).

2. The complex as claimed in claim 1, wherein the polysaccharide has the structure of formula I:

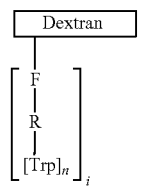

Formula I wherein
n represents the mole fraction of R substituted with Trp and is between 0.2 and 0.7,
i represents the mole fraction of acid functions borne by the group R per saccharide unit and is between 0.5 and 2, when R is not substituted with Trp, then the acid(s) of the group R are carboxylates of a cation.

3. The complex as claimed in claim 2, wherein F is an ester, a carbonate, carbamate or an ether.

4. The complex as claimed in claim 2, wherein F-R is represented by:

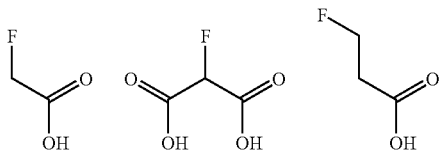

or alkali metal cation salts thereof.

5. The complex as claimed in claim 1, wherein the polysaccharide/HBP ratio is between 0.5 and 500.

6. The complex as claimed in claim 1, wherein the polysaccharide/HBP ratio is between 0.5 and 100.

7. The complex as claimed in claim 1, wherein the HBP is selected from the group consisting of human growth hormone (hGH) and parathyroid hormone (PTH).

8. The complex as claimed in claim 1, wherein the HBP is selected from the group consisting of transforming growth factor β1 and 2 (TGF-β), insulin-like growth factor 2 (IGF-2), heparin binding EGF-like growth factor (HB-EGF), fibroblasts growth factors 1 to 14 (FGF), keratinocyte growth factor (KGF), nerve growth factor beta (NGF-beta), connective tissue growth factor (CTGF), placental growth factor (PIGF), R-spondins 1 to 4 and vascular endothelial growth factors A and B (VEGF).

9. A pharmaceutical composition comprising a complex as claimed in claim 1.

10. The pharmaceutical composition as claimed in claim 9, wherein it is obtained by drying and/or lyophilization.

11. A method of forming the complex of claim 1, comprising: forming a complex between the HBP and the polysaccharide by simple mixing of an aqueous solution of the HBP and an aqueous solution of the polysaccharide at room temperature, without addition of organic solvent.

12. The method of claim 11, wherein the aqueous solution of the polysaccharide is formed by
dissolving a lyophilizate of the polysaccharide in water at room temperature.

* * * * *